(12) United States Patent
Zumbrum et al.

(10) Patent No.: US 11,421,806 B1
(45) Date of Patent: Aug. 23, 2022

(54) FLUID TRANSFER CONNECTOR

(71) Applicant: Sartorius Stedim North America Inc., Bohemia, NY (US)

(72) Inventors: Michael Zumbrum, New Oxford, PA (US); William Kimmick, Mechanicsburg, PA (US)

(73) Assignee: Sartorius Stedim North America Inc., Bohemia, NY (US)

( * ) Notice: Subject to any disclaimer, the term of this patent is extended or adjusted under 35 U.S.C. 154(b) by 0 days.

(21) Appl. No.: 17/218,396

(22) Filed: Mar. 31, 2021

(51) Int. Cl.
*F16L 33/213* (2006.01)
*B67D 7/38* (2010.01)

(52) U.S. Cl.
CPC .............. *F16L 33/213* (2013.01); *B67D 7/38* (2013.01)

(58) Field of Classification Search
CPC .................................. F16L 33/213; B67D 7/38
USPC ......................................... 285/59, 60, 148.2
See application file for complete search history.

(56) References Cited

U.S. PATENT DOCUMENTS

| | | | | |
|---|---|---|---|---|
| 3,646,935 A * | 3/1972 | Holbrook | ............ | A61M 1/0001 604/319 |
| 4,236,736 A * | 12/1980 | Anderson | ................ | F16L 47/32 285/125.1 |
| 4,398,757 A * | 8/1983 | Floyd | .................... | F16L 37/133 285/315 |
| 4,934,745 A * | 6/1990 | Healy | .................... | F16L 33/227 285/255 |
| 5,047,021 A * | 9/1991 | Utterberg | ................ | F16L 33/24 604/533 |
| 5,335,943 A * | 8/1994 | Duryea | .................... | F16L 33/00 285/12 |
| 5,988,700 A * | 11/1999 | Prichard | ................ | F16L 25/14 285/148.23 |
| 7,185,681 B2 * | 3/2007 | Romano | ................... | A61J 1/05 141/100 |
| 8,690,815 B2 * | 4/2014 | Porter | ................. | A61M 1/3661 604/6.16 |
| 10,994,117 B2 * | 5/2021 | Her | ....................... | A61M 39/12 |
| 2008/0309073 A1 * | 12/2008 | Bach | ..................... | F16L 33/225 285/222.1 |
| 2010/0215430 A1 * | 8/2010 | Carrier | ................ | F16L 33/2073 403/408.1 |

OTHER PUBLICATIONS

Qosina, Qosina Introduces New 2018 Catalog, Oct. 12, 2017, Straight Connectors Reduced (27232).*
Qosina 2018 Catalog, connectors, known at least as early as Mar. 2021, 2 pgs.

* cited by examiner

*Primary Examiner* — Timothy L Maust
(74) *Attorney, Agent, or Firm* — Womble Bond Dickinson (US) LLP

(57) ABSTRACT

A fluid connector includes a body that has a first end and a second end. The first end defines a first opening that has a first diameter and the second end defines a second opening that has a second diameter different from the first diameter. The body has an inner surface defining a channel that extends from the first opening to the second opening. The inner surface smoothly extending from the first end to the second end. The first connector configured to prevent foaming of media flowed therethrough as a flow diameter of the media transition from the first diameter to the second diameter.

18 Claims, 5 Drawing Sheets

FLUID TRANSFER CONNECTOR

BACKGROUND

1. Technical Field

The present disclosure relates to fluid transfer connectors and, more specifically, to fluid transfer connectors with an inlet diameter different from an outlet diameter thereof.

2. Discussion of Related Art

Biopharmaceutical and pharmaceutical drug developers and manufactures often develop and manufacture products in a fluid form. These products must be handled with care to maintain an aseptic environment and avoid contamination. Drugs developed and produced by biopharmaceutical and pharmaceutical companies are often produced through a multitude of steps that may require transfer of the drugs or media in fluid form through conduits for purposes of sampling, packaging, mixing, separating, or passing between stations for various steps of the manufacturing process.

As the media is transferred through fluid conduits, it may be necessary to change a diameter of the fluid conduit such that a flow diameter of the media within the fluid conduits changes. In addition, as media is transferred into a vessel with a diameter different from the fluid conduit providing the media, the flow diameter of the media may change as it enters the vessel.

When the flow diameter of a media changes, properties of the media may change. For example, a pressure of the media may change. In some instances, the media may foam at the transition of the flow diameter. The changes in the properties of the media may make it difficult to accurately or precisely measure an amount of media flowed through a system or into a vessel.

SUMMARY

This disclosure relates generally to fluid connectors having an inlet diameter and an outlet diameter that is different from the inlet diameter. The fluid connectors disclosed herein include a smooth transition between the inlet diameter and the outlet diameter such that fluids flow through and exit the fluid connector without foaming or other detrimental changes in the properties of the fluid.

In an embodiment of the present disclosure, a fluid connector includes a body that has a first end and a second end. The first end defines a first opening that has a first diameter and the second end defines a second opening that has a second diameter different from the first diameter. The body has an inner surface defining a channel that extends from the first opening to the second opening. The inner surface smoothly extending from the first end to the second end. The first connector configured to prevent foaming of media flowed therethrough as a flow diameter of the media transition from the first diameter to the second diameter.

In embodiments, the second diameter is larger than the first diameter. The second diameter may be in a range of 1.5 to 4 times larger than the first diameter. The second diameter may be twice the first diameter. The first diameter may be 0.125 inches and the second diameter may be 0.25 inches.

In some embodiments, the body includes a first end portion that terminates at the first end, the first end portion may include a securement means configured to secure a fluid conduit thereabout. The securement means may be a barb.

In certain embodiments, the body may include a first rib that extends from an outer surface of the body. The first rib may be configured to abut an end of a fluid conduit secured to the first end portion. The body may include a second end portion that terminates at the second end that has a second rib extending from the outer surface of the body. The second rib may be configured to abut an end of a fluid conduit, a vessel cap, or a vessel stopper secured to the second end portion.

In particular aspects, the body has an outer surface and an inner surface in the first end portion. A wall thickness of the body defined between the outer surface and the inner surface may be substantially constant in the first end portion. The outer surface of the body may have a constant diameter in the second end portion. The channel of the body may have a frustoconical shape.

In another embodiment of the present disclosure, a system includes a connector, a first fluid conduit, and a second fluid conduit, a vessel stopper, or a vessel cap that has a body including a first end that defines a first opening that has a first diameter. The body also has a second end that defines a second opening that has a second diameter different from the first diameter. The body has an inner surface which defines a channel that extends from the first opening to the second opening. The inner surface smoothly extends from the first end to the second end. The first fluid conduit is secured to the first end of the connector. The second fluid conduit, vessel stopper, or vessel cap is secured to the second end of the connector. The connector is configured to prevent foaming of media flowed therethrough as a flow diameter of the media transitions from the first diameter to the second diameter.

In embodiments, the vessel stopper or the vessel cap is secured to the second end of the connector, the vessel stopper or the vessel cap is secured to a vessel such that the second opening of the connector is in an interior of the vessel. The connector may be configured to prevent foaming of media flowing through the first fluid conduit and into the interior of the vessel.

In some embodiments, the second fluid conduit is secured to the second end of the connector. The second fluid conduit may have a diameter larger than the first fluid conduit.

In another embodiment of the present disclosure, a method of filling a vessel with media includes securing a first fluid conduit to a first end portion of a connector and flowing media through the first fluid conduit. The first fluid conduit has a first diameter. Flowing the media through the first fluid conduit includes the media flowing through the connector from a first end of the connector to a second end of the connector. The connector defines a channel having the first diameter at the first end of the connector and a second diameter at the second end of the connector that is different form the first diameter. The channel smoothly transitions from the first diameter to the second diameter between the first end and the second end of the connector such that foaming of the media is prevented as a flow diameter of the media changes between the first end and the second end of the connector.

In embodiments, the method includes securing the second end of the connector to a second fluid conduit having a diameter different from the first fluid conduit. Alternatively, the method may include securing the second end of the connector to a vessel stopper or a vessel cap. The method may include securing the vessel stopper or the vessel cap to a vessel defining an interior. Flowing the media into the connector may include measuring an amount of media flowed into the interior of the vessel. The connector may increase an accuracy of an amount of media flowed into the vessel.

Further, to the extent consistent, any of the embodiments or aspects described herein may be used in conjunction with any or all of the other embodiments or aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
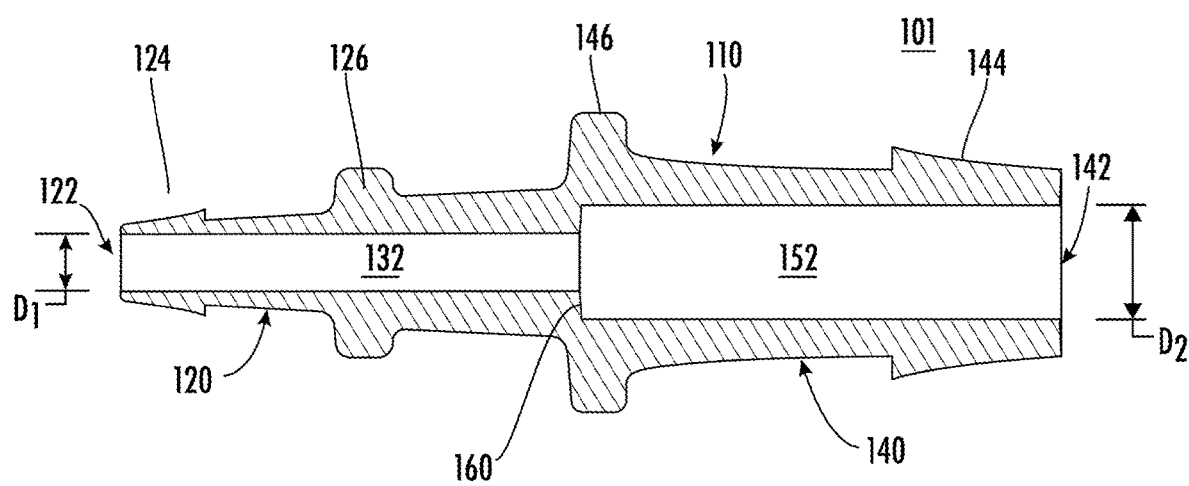
FIG. 1 is a longitudinal cross-sectional view of a prior art fluid connector.

The present disclosure will now be described more fully hereinafter with reference to example embodiments thereof with reference to the drawings in which like reference numerals designate identical or corresponding elements in each of the several views. These example embodiments are described so that this disclosure will be thorough and complete, and will fully convey the scope of the disclosure to those skilled in the art. Features from one embodiment or aspect can be combined with features from any other embodiment or aspect in any appropriate combination. For example, any individual or collective features of method aspects or embodiments can be applied to apparatus, product, or component aspects or embodiments and vice versa. The disclosure may be embodied in many different forms and should not be construed as limited to the embodiments set forth herein; rather, these embodiments are provided so that this disclosure will satisfy applicable legal requirements. As used in the specification and the appended claims, the singular forms "a," "an," "the," and the like include plural referents unless the context clearly dictates otherwise. In addition, while reference may be made herein to quantitative measures, values, geometric relationships or the like, unless otherwise stated, any one or more if not all of these may be absolute or approximate to account for acceptable variations that may occur, such as those due to manufacturing or engineering tolerances or the like.

Referring now to FIG. 1, a prior art fluid connector is illustrated and is generally referred to as connector 101. The connector 101 includes a body 110 that includes a first end portion 120 and a second end portion 140 opposite the first end portion 120. The first end portion 120 defines a first opening 122 having a first diameter $D_1$ and the second end portion 140 defines a second opening 142 having a second diameter $D_2$ different from the first diameter $D_1$. The first opening 122 may be an inlet or an outlet with the second opening 142 being the other of the inlet or the outlet.

The first end portion 120 is configured to be received within a lumen of a first fluid conduit having a first diameter substantially equal to the diameter of the first opening 122. The first end portion 120 includes a securement means such as a barb 124 that secures the first fluid conduit to the body 110 of the fluid connector 101. The first end portion 120 may also include a rib or stop 126 that is configured to abut an end of the first fluid conduit. In some embodiments, the first end portion 120 may be received in a vessel stopper or cap in an end of a vessel such that the first opening 122 is in fluid communication with an interior of the vessel.

Similarly, the second end portion 140 is configured to be received within a lumen of a second fluid conduit having a second diameter substantially equal to the diameter of the second opening 142. The second end portion 140 includes a securement means such as a barb 144 that secures the second fluid conduit to the body 110 of the fluid connector 101. The second end portion 140 may also include a rib or stop 146 that is configured to abut an end of the second fluid conduit. In some embodiments, the second end portion 140 may be received in a vessel stopper or cap in an end of a vessel such that the second opening 142 is in fluid communication with an interior of the vessel.

The first end portion 120 defines a first channel 132 having a substantially constant diameter that is substantially equal to the first diameter $D_1$. The second end portion 140 defines a second channel 152 having a substantially constant diameter that is substantially equal to the second diameter $D_2$. The first channel 132 extends to the second channel 152 and meets the second channel 152 at a transition 160. As shown, the transition 160 is abrupt, however, there may be a slight taper or chamfer at the transition 160 between the first channel 132 or the second channel 152. This abrupt transition 160 has been shown to create foaming in media flowing through the connector 101. This foaming may make it difficult to accurately or precisely measure an amount of media flowing through the connector 101. Moreover, the transition 160 may make it difficult to measure a flow of a non-Newtonian fluids such as rheopectic fluids. For example, an rheopectic fluid may create a backpressure within the connector 101 such that an amount of media flowing through the connector 101 is less than anticipated.

Figure 6:
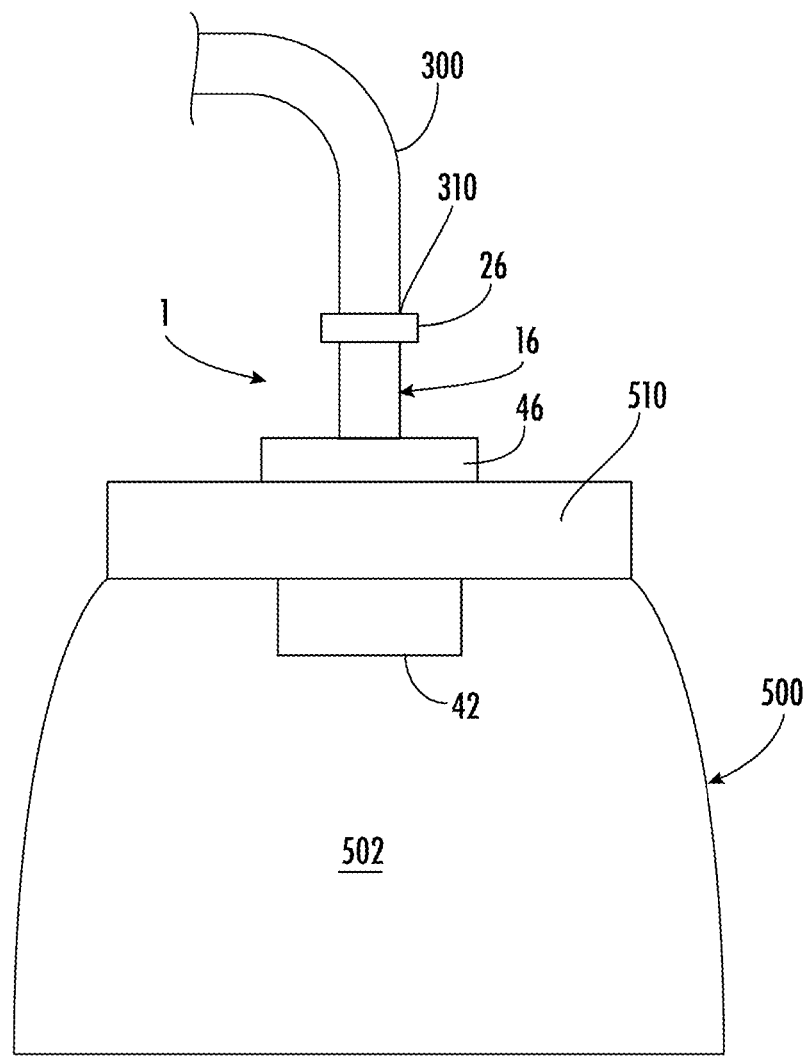
FIG. 6 is a perspective view of the fluid connector of FIG. 2 with a fluid conduit secured to a first end of the fluid connector and the second end of the fluid connector secured in a vessel stopper of a vessel.

While the connector 101 is shown as a standalone connector, similar effects have been shown when a conduit is connected to a stopper with an opening of the stopper open to the interior of the vessel with an abrupt transition as shown in FIG. 6.

Figure 2:
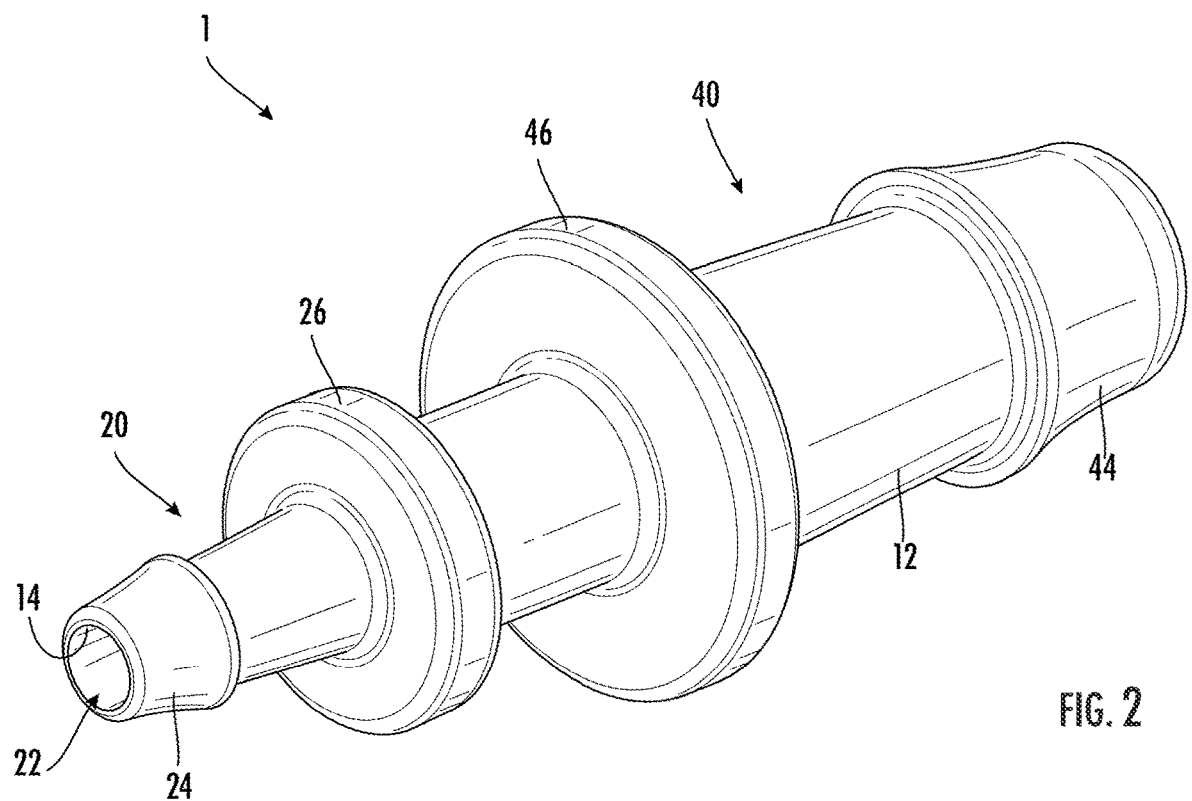
FIG. 2 is a perspective view of a fluid connector provided in accordance with an embodiment of the present disclosure.
Figure 3:
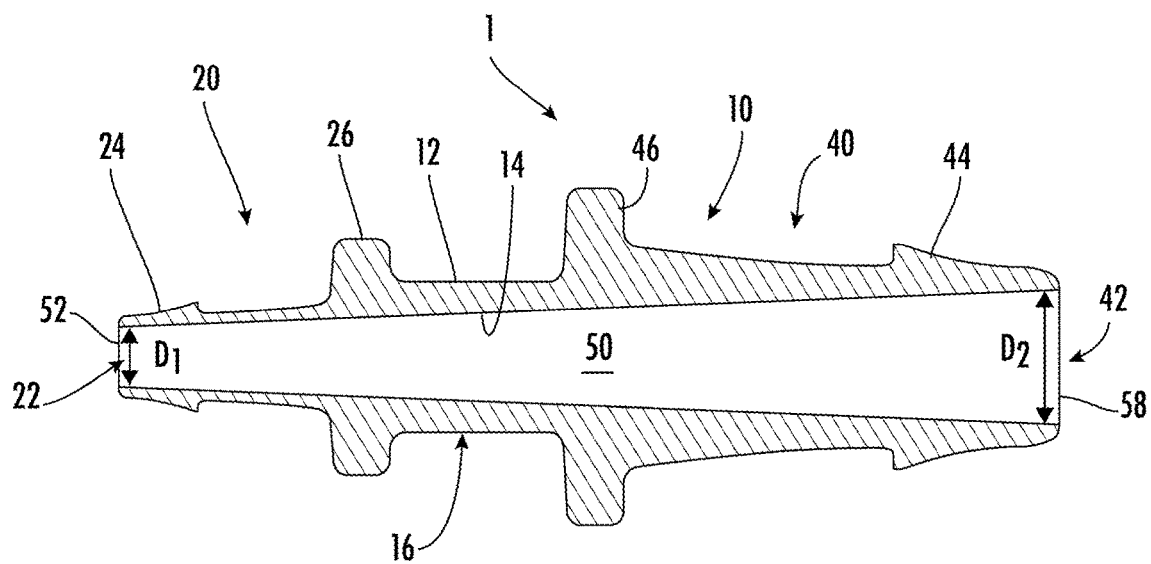
FIG. 3 is a longitudinal cross-sectional view of the fluid connector of FIG. 2.

Referring now to FIGS. 2 and 3, a fluid connecter provided in accordance with an embodiment of the present disclosure is generally referred to as connector 1. The connector 1 is configured to smoothly transition a flow diameter of media flowing through a fluid conduit from a first diameter to a second diameter. The smooth transition of the flow diameter of the connector 1 avoids foaming and other changes in properties of media flowing through the connector 1 as compared to the prior art connector 101 described above. As such, the accuracy and the precision of measuring an amount of media flowing through the connector 1 is significantly greater when compared to an accuracy and precision of measuring an amount of media flowing through the prior art connector 101.

The connector 1 includes a body 10 that includes a first end portion 20 and a second end portion 40 opposite the first end portion 20. The first end portion 20 defines a first opening 22 having a first diameter $D_1$ and the second end portion 40 defines a second opening 42 having a second diameter $D_2$ different from the first diameter $D_1$. The first opening 22 may be an inlet or an outlet with the second opening 42 being the other of the inlet or the outlet.

The body 1 defines a channel 50 that extends from the first opening 22 to the second opening 42 with the diameter of the channel 50 linearly increasing from the first opening 22 to the second opening 42. Specifically, a first end 52 of the channel 50 at the first opening 22 has a diameter $D_1$ and the second end 58 of the channel 50 at the second opening 42, opposite the first end 52, has a diameter $D_2$. As shown, the channel 50 has a frustoconical shape. In embodiments, the diameter of the channel 50 may increase in a nonlinear but smooth manner. The channel 50 is configured to transition a flow diameter of media entering the body 1 from one flow diameter, e.g., diameter $D_1$ to another flow diameter, e.g., diameter $D_2$, in a smooth manner. This smooth transition of the flow diameter of the media within the body 10 of the connector 1 maintains a smooth or laminar flow of the fluid and reduces or prevents foaming of the media as the flow diameter changes. The diameter $D_2$ may be in a range of 1.5 to 4 times greater than the diameter $D_1$. For example, the diameter $D_1$ may be half of the diameter $D_2$. In some embodiments, the diameter $D_1$ may be 0.125 inches and the diameter $D_2$ may be 0.25 inches. the diameter $D_1$ may be 0.125 inches and the diameter $D_2$ may be 0.5 inches. In particular embodiments, the diameter $D_1$ may be in a range of 0.09375 inches to 2.0 inches (e.g., 0.09375, 0.125, 0.1875, 0.25, 0.375, 0.5, 0.625, 0.75, 0.875, 1, or 2 inches) and the diameter $D_2$ may be in a range of 0.1875 to 4 inches (e.g., 0.1875, 0.25, 0.375, 0.5, 0.625, 0.75, 0.875, 1, 1.25, 1.5, 1.75, 2, 2.5, 3, 3.5, or 4 inches).

Figure 4:
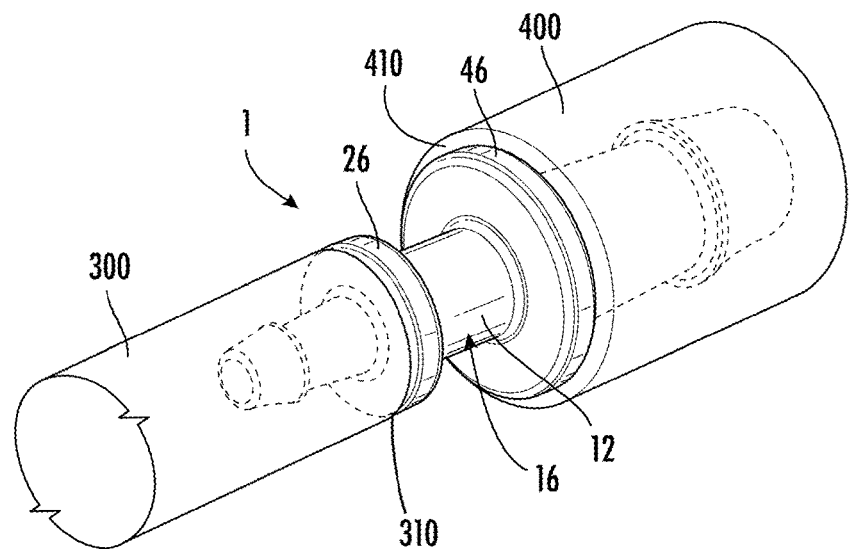
FIG. 4 is a perspective view of the fluid connector of FIG. 2 with a first conduit and a second conduit secured to the ends of the fluid connector.
Figure 5:
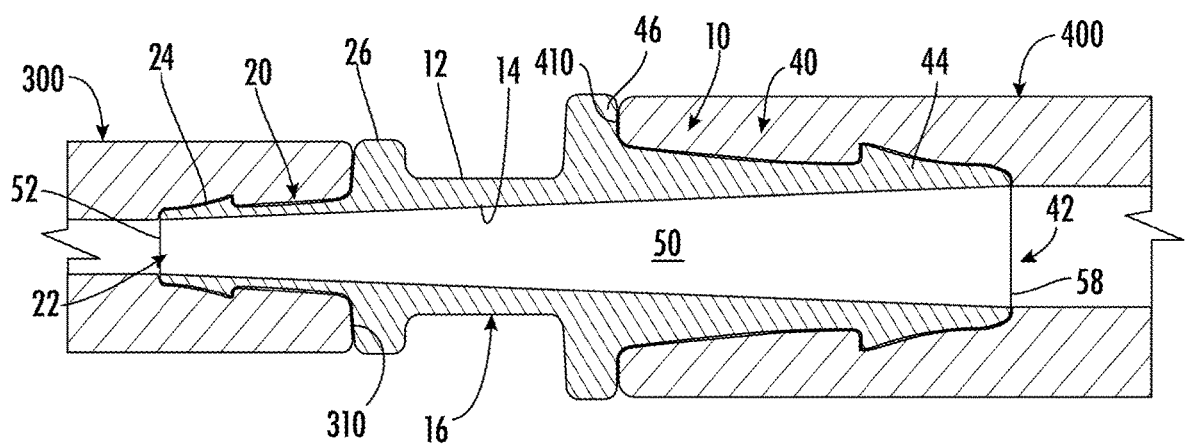
FIG. 5 is a longitudinal cross-sectional view of the fluid connector of FIG. 4.

With additional reference to FIGS. 4 and 5, the first end portion 20 is received within a lumen of a first fluid conduit 300 having a first flow diameter substantially equal to the diameter of the first opening 22. The first end portion 20 may be tapered from the first opening 22 towards the second opening 42 such that a wall thickness defined from an outer surface 12 of the body 10 to an inner surface 14 of the body 10, which defines the channel 50, is substantially constant from the first opening 22 to the second end portion 40

The first end portion 20 may include a securement means such as a barb 24 that secures the first fluid conduit 300 to the body 10 of the fluid connector 1. In some embodiments, the first end portion 20 may include securement means in the form of a luer connector or a high friction outer surface. In certain embodiments, the first end portion 20 may be provided without a securement means. The first end portion 20 may also include a rib or stop 26 that is configured to abut an end 310 of the first fluid conduit 300 when the first fluid conduit 300 is secured to the fluid connector 1.

The second end portion 40 may be configured to be received within a lumen of a second fluid conduit 400 having a second flow diameter substantially equal to the diameter of the second opening 42. The outer surface 12 of the body 10 may have a substantially constant diameter in the second end portion 40. As such, a wall thickness defined between the outer surface 12 and the inner surface 14 of the second end portion may decrease as the second end portion 40 extends away from the first end portion 20.

The second end portion 40 may include a securement means such as a barb 44 that secures the second end portion 40 to a second fluid conduit 400. In some embodiments, the second end portion 40 may include securement means in the form of a luer connector or a high friction outer surface. The securement means of the second end portion 40 may be the same or different from the securement means of the first end portion 20. In certain embodiments, the second end portion 40 may be provided without a securement means. The second end portion 40 may also include a rib or stop 46 that is configured to abut an end 410 of the second fluid conduit 400, vessel stopper or cap. The rib or stop 46 extends from the outer surface 12 of the body 10.

The body 10 may include a central portion 16 that is positioned between the first and second end portions 20, 40. The central portion 16 may be positioned between the rib 26 of the first end portion 20 and the rib 46 of the second end portion 40. The outer surface 12 may have a substantially constant diameter in the central portion 16 that is equal to or less than a diameter of the outer surface 12 in the second end portion 40. In some embodiments, the outer surface 12 in the central portion 16 may be tapered such that a wall thickness defined between the outer surface 12 and the inner surface 14 may be constant in the central portion 16.

With continued reference to FIGS. 4 and 5, the first end portion 20 of the connector 1 is received in an end 310 of a first fluid conduit 300 and the second end portion 40 of the connector 1 is received in an end 410 of a second fluid conduit 400. The first fluid conduit 300 may have an inner flow diameter substantially equal to a diameter of the first opening 22 of the connector 1 and the second fluid conduit 400 may have an inner flow diameter substantially equal to a diameter of the second opening 42 of the connector 1. The connector 1 smoothly transitions the flow diameter of a media flowing therethrough from the flow diameter of the first fluid conduit 300 to the flow diameter of the second fluid conduit 400, or vice versa depending on flow direction. This smooth transition of the flow diameter prevents foaming or other undesirable effects within media flowing through the connector 1. The prevention of foaming may increase an accuracy and precision of a measurement of an amount of the media flowing through the connector 1 when compared to a measurement of the connector 101 detailed above.

The first fluid conduit 300 may be secured to the first end portion 20 by the barb 24 or other securement means. The first fluid conduit 300 may be positioned over the first end portion 20 such that an end 310 of the first fluid conduit 300 abuts the rib 26. The second fluid conduit 400 may be secured to the second end portion 40 by the barb 44 or other securement means. The second fluid conduit 400 may be positioned over the second end portion 40 such that an end 410 of the second fluid conduit 400 abuts the rib 46.

With reference to FIG. 6, the first end portion 20 of the connector 1 may be secured to a first fluid conduit 300, as detailed above, and the second end portion 40 may be secured to a vessel stopper or cap 510 of a vessel 500. Specifically, as shown, the second end portion 40 of the connector 1 may be received in the vessel stopper or cap 510 of a vessel 500 such that the first fluid conduit 300 secured to the first end portion 20 is in fluid communication with an interior 502 of the vessel through the connector 1. The second end portion 40 may extend through the vessel stopper or cap 510 such that second opening 42 of the second end portion 40 is at least partially disposed within the interior 502 of the vessel 500. The smooth transition of the flow diameter of media through the connector 1 may reduce or eliminate foaming of the media as the media enters the interior 502 of the vessel 500. The reduction in foaming may increase an accuracy or precision of a fill measurement of the vessel 500 with the media.

Figure 7:
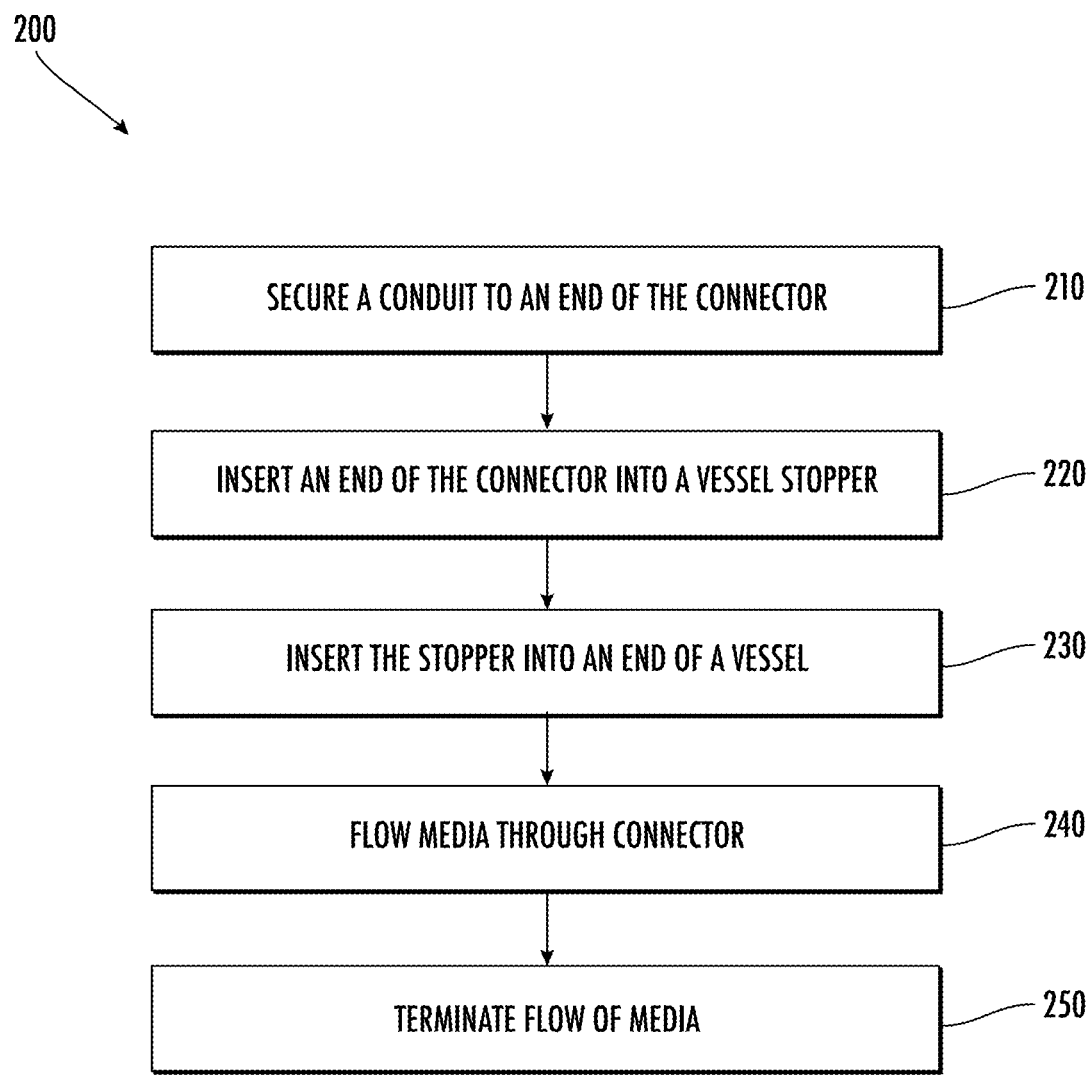
FIG. 7 is a flowchart of a method of flowing media in accordance with an embodiment of the present disclosure.

Referring now to FIG. 7, a method of filling a vessel with media is described in accordance with an embodiment of the present disclosure is referred to generally as method 200 with reference to the fluid connector 1 of FIGS. 2 and 3 and the system including a fluid conduit 300 and a vessel 500 of FIG. 6. The fluid conduit 300 is secured to the first end portion 20 of the connector 1 by inserting the first end portion 20 into an end of the fluid conduit 300 until the end 310 of the fluid conduit 300 abuts the rib 26 of the connector 1 (Step 210). A securement means, e.g., barb 24, of the first end portion 20 may secure the fluid conduit 300 to the connector 1. The second end portion 40 is inserted into an aperture of a vessel cap or stopper 510 of a vessel 500 until the vessel cap or stopper 510 abuts the rib 46 (Step 220). A securement means, e.g., barb 44, may secure the connector 1 to the cap or stopper 510. The vessel cap or stopper 510 is secured to the vessel 500 before or after the connector 1 is secured to the vessel cap or stopper 510 (Step 230).

When the fluid conduit 300 is secured to the connector 1 and the connector 1 is secured to the vessel 500, the fluid conduit 300 is in fluid communication with an interior 502 of the vessel 500, a flow of media is provided through the fluid conduit 300 and into the interior 502 of the vessel 500 through the connector 1 (Step 240). The flow of media may be controlled manually or by a controller. The flow of media may be under the influence of gravity and/or as a result of a pump pumping the media. As the media flows into the interior 502 of the vessel 500, the amount of media is measured upstream of the connector 1. When a desired amount of media is flowed into the interior 502 of the vessel 500, the flow of media is terminated (Step 250). The smooth transition of the channel 50 from the first diameter of the first opening 22 to the second diameter of the second opening 42 prevents the media from foaming as the flow diameter of the media increases through the connector 1 and from the connector 1 into the interior 502 of the vessel 500. This reduction or elimination of foaming increases the accuracy of the measurement of the media flowed into the vessel 500 when compared to previous connectors, e.g., connector 101 (FIG. 1).

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A fluid connector comprising:
a body having a first end defining a first opening having a first diameter and a second end defining a second opening having a second diameter in a range of 1.5 to 4 times larger than the first diameter, the body having an inner surface defining a channel extending from the first opening to the second opening, the inner surface smoothly extending and continually increasing in diameter from the first end to the second end, the fluid connector configured to prevent foaming of media flowed therethrough as a flow diameter of the media transitions from the first diameter to the second diameter, the body having an outer surface opposite the inner surface, the outer surface including a first barb adjacent the first end over the channel configured to secure a first conduit about the outer surface.

2. The fluid connector according to claim 1, wherein the second diameter is twice the first diameter.

3. The fluid connector according to claim 1, wherein the first diameter is 0.125 inches and the second diameter is 0.25 inches.

4. The fluid connector according to claim 1, wherein the body includes a first end portion that terminates at the first end, the first end portion including the first barb thereabout.

5. The fluid connector according to claim 1, wherein the body includes a first end portion that terminates at the first end having a first rib extending from the outer surface of the body, the first rib configured to abut an end of a fluid conduit secured to the first end portion.

6. The fluid conduit according to claim 5, wherein the body includes a second end portion that terminates at the second end having second rib extending from the outer surface of the body, the second rib configured to abut an end of a fluid conduit, a vessel stopper, or a vessel cap secured to the second end portion.

7. The fluid connector according to claim 1, wherein the body includes a first end portion that terminates at the first end, a wall thickness of the body defined between the outer surface and the inner surface being substantially constant in the first end portion.

8. The fluid connector according to claim 1, wherein the body includes a second end portion that terminates at the second end, the outer surface having a constant diameter in the second end portion.

9. The fluid connector according to claim 1, wherein the channel has a frustoconical shape.

10. A system comprising:
a connector comprising a body having a first end defining a first opening having a first diameter and a second end defining a second opening having a second diameter in a range of 1.5 to 4 times larger than the first diameter, the body having an inner surface defining a channel extending from the first opening to the second opening, the inner surface smoothly extending and continually increasing in diameter from the first end to the second end, the body having an outer surface opposite the inner surface, the outer surface including a first barb adjacent the first end over the channel;
a first fluid conduit secured to the first end of the connector via the first barb; and
a second fluid conduit, a vessel stopper, or a vessel cap secured to the second end of the connector, the connector configured to prevent foaming of media flowed therethrough as a flow diameter of the media transitions from the first diameter to the second diameter.

11. The system according to claim 10, wherein the vessel stopper or the vessel cap is secured to the second end of the connector, the vessel stopper or the vessel cap secured to a vessel such that the second opening of the connector is in an interior of the vessel, the connector configured to prevent foaming of media flowing through the first fluid conduit into the interior of the vessel.

12. The system according to claim 10, wherein the second fluid conduit is secured to the second end of the connector.

13. A method of filling a vessel with media, the method comprising:
securing a first fluid conduit to a first end portion of a connector via a first barb on an outer surface of the first end portion, the first fluid conduit having a first diameter; and
flowing media through the first fluid conduit into the connector such media flows through the connector from a first end of the connector to a second end of the connector, the connector defining a channel having the first diameter at the first end of the connector and a second diameter at the second end of the connector in a range of 1.5 to 4 times larger than the first diameter, the channel continually increasing in diameter and smoothly transitioning from the first diameter to the second diameter between the first end and the second end of the connector such that foaming of the media is prevented as a flow diameter of the media changes between the first end and the second end of the connector.

14. The method according to claim 13, further comprising securing the second end of the connector to a second fluid conduit having a diameter different from the first fluid conduit.

15. The method according to claim 13, further comprising securing the second end of the connector to a vessel stopper or a vessel cap.

16. The method according to claim 15, further comprising securing the vessel stopper or the vessel cap to a vessel defining an interior.

17. The method according to claim 16, wherein flowing the media into the connector includes measuring an amount of media flowed into the interior of the vessel, the connector increasing an accuracy of an amount of media flowed into the vessel.

18. The fluid connector according to claim 1, wherein the second diameter is in a range of 2 to 4 times larger than the first diameter.

* * * * *